(12) United States Patent
Bodor

(10) Patent No.: US 7,560,448 B2
(45) Date of Patent: Jul. 14, 2009

(54) ENHANCEMENT OF ACTIVITY AND/OR DURATION OF ACTION OF SOFT ANTI-INFLAMMATORY STEROIDS FOR TOPICAL OR OTHER LOCAL APPLICATION

(76) Inventor: Nicholas S. Bodor, 3929 SW. 69th Ave., Gainesville, FL (US) 32608

( * ) Notice: Subject to any disclaimer, the term of this patent is extended or adjusted under 35 U.S.C. 154(b) by 932 days.

(21) Appl. No.: 10/868,966

(22) Filed: Jun. 17, 2004

(65) Prior Publication Data
US 2005/0026892 A1 Feb. 3, 2005

Related U.S. Application Data

(60) Provisional application No. 60/479,496, filed on Jun. 19, 2003.

(51) Int. Cl.
*A61K 31/56* (2006.01)
(52) U.S. Cl. ...................... 514/170; 514/171
(58) Field of Classification Search ............. 514/171, 514/170
See application file for complete search history.

(56) References Cited

U.S. PATENT DOCUMENTS

| | | | |
|---|---|---|---|
| 3,828,080 A | 8/1974 | Phillipps et al. | |
| 4,285,937 A | 8/1981 | Kalvoda | |
| 4,710,495 A | 12/1987 | Bodor | |
| 4,996,335 A | 2/1991 | Bodor | |
| 5,916,550 A | 6/1999 | Inada et al. | |
| 5,981,517 A * | 11/1999 | Bodor | 514/181 |
| 6,368,616 B1 * | 4/2002 | Doi | 424/434 |
| 2002/0028193 A1 | 3/2002 | Cornett et al. | |

FOREIGN PATENT DOCUMENTS

GB 1384372 2/1975

WO 97/42214 A1 11/1997

OTHER PUBLICATIONS

Bausch & Lomb: "Lotemax" Online. URL:http://www.bausch.com/us/resource/pharma/lotemax.jsp, retrieved on Oct. 8, 2004.
Druzgala et al., *J. Steroid Biochem. Molec. Biol.*, vol. 38, No. 2, pp. 149-154, published by Pergamon Press plc, Kidlington, Oxford, UK (1991).

* cited by examiner

*Primary Examiner*—San-ming Hui
(74) *Attorney, Agent, or Firm*—Buchanan Ingersoll & Rooney PC

(57) ABSTRACT

Methods and compositions for enhancing the activity and/or duration of action of loteprednol etabonate and other soft anti-inflammatory steroids of the haloalkyl 17α-alkoxycarbonyloxy-11β-hydroxyandrost-4-en-3-one-17β-carboxylate type and the corresponding $\Delta^{1,4}$-compounds are described. The enhancing agents have the formula:

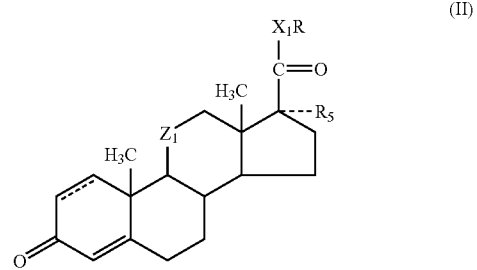

(II)

wherein R is H or $C_1$-$C_4$ alkyl; $Z_1$ is carbonyl or β-hydroxymethylene; $X_1$ is —O— or —S—; $R_5$ is —OH, —$OR_6$, —$OCOOR_6$ or —$OCOR_7$ wherein $R_6$ is $C_1$-$C_4$ alkyl and $R_7$ is $C_1$-$C_4$ alkyl, fluoromethyl or chloromethyl; and the dotted line in ring A indicates that the 1,2-linkage is saturated or unsaturated; with the proviso that when R is $C_1$-$C_4$ alkyl, then $R_5$ is —OH.

28 Claims, No Drawings

ENHANCEMENT OF ACTIVITY AND/OR DURATION OF ACTION OF SOFT ANTI-INFLAMMATORY STEROIDS FOR TOPICAL OR OTHER LOCAL APPLICATION

CROSS-REFERENCE TO RELATED APPLICATION

This application claims the benefit of U.S. Provisional Patent Application No. 60/479,496, filed Jun. 19, 2003, incorporated by reference herein in its entirety and relied upon.

BACKGROUND OF THE INVENTION

1. Technical Field

The invention relates to enhancing the activity and/or the duration of action of soft anti-inflammatory steroids for topical or other local application.

2. Background Art

Topical or other local application of potent glucocorticoids can produce severe toxic effects such as Cushingoid features, pituitary-adrenal suppression, skin atrophy, immunosuppression, weight gain and inhibition of wound healing. Other kinds of toxic responses, including allergies and cataracts, have resulted from long term use of drugs of this type.

Ophthalmic application of glucocorticosteroids presents additional problems. The protective mechanisms built into the eye allow only small amounts of doses applied to the eye to reach the target sites within the eye; generally, over 90 percent of the total dose will find its way into the general circulation. This in turn leads to serious systemic side effects of the type described above. Moreover, there is a more serious and specific side effect when these drugs are used in the eye, which is an increase in intraocular pressure (IOP). Corticosteroid-induced chronic or acute glaucoma has in fact been reported since the early 1960's. Generally, the corticosteroid is needed only topically to control the inflammation. However, the absorbed steroid is responsible for the serious side effects noted above. It is believed that the effect of the corticosteroid on the aqueous outflow pathway and adjacent tissue glycosaminoglycans (GAG's) is important in the development of glucocorticoid-induced ocular hypertension.

The natural glucocorticosteroids and many of their marketed derivatives are $\Delta^4$ and $\Delta^{1,4}$ pregnenes having 21-hydroxy substituents. There are, however, a number of anti-inflammatory $\Delta^4$ and $\Delta^{1,4}$ androstenes described in the literature; note, for example, British Patent Specification No. 1,384,372; Phillipps et al. U.S. Pat. No. 3,828,080 and Kalvoda et al. U.S. Pat. No. 4,285,937.

In recent years, soft steroids have been developed in an effort to provide compounds having potent anti-inflammatory activity with minimal systemic activity. One series of soft steroids which is described as having potent anti-inflammatory activity with minimal systemic activity consists of the 17α-carbonates of Bodor U.S. Pat. No. 4,996,335. These compounds include as preferred embodiments haloalkyl 17α-alkoxycarbonyloxy-11β-hydroxyandrost-4-en-3-one-17β-carboxylates and the corresponding $\Delta^{1,4}$ compounds, optionally bearing 6α- and/or 9α-fluorine and 16α- or 16β-methyl substituents. One of these compounds is chloromethyl 17α-ethoxycarbonyloxy-11β-hydroxyandrosta-1,4-dien-3-one-17α-carboxylate, also known as loteprednol etabonate. Loteprednol etabonate is presently marketed in the United States by Bausch & Lomb Pharmaceuticals, Inc. as Alrex® and Lotemax® for ophthalmic use. Other uses of loteprednol etabonate are currently in clinical trials.

Despite the development of steroids having less systemic toxicity, however, there is a serious need for improvement in topical and other local applications. The newer, less toxic, locally/topically active compounds are more expensive to synthesize than the long-established compounds. Moreover, the most potent anti-inflammatory steroids are those which have substitution at the 6, 9 and/or 16-positions and thus also not only are farthest removed structurally from the natural corticosteroids but also have the greatest toxicity. Thus, there is a need for enhancing the activity or duration of action or both of the 17α-carbonate type soft androstenes which lack the 6-, 9- and/or 16-substitution pattern. Further, it would be desirable to allow these steroids to undergo easier metabolism and concentrate them at the desired site of action.

One of the major, inactive metabolites of hydrocortisone is cortienic acid, i.e. 11β,17α-dihydroxyandrost-4-en-3-one-17β-carboxylic acid. Cortienic acid and the corresponding $\Delta^{1,4}$ acid have been previously described as synthetic intermediates useful in the preparation of the soft steroids described in Bodor U.S. Pat. Nos. 4,710,495 and 4,996,335. The 17β-methyl, ethyl and isopropyl esters of $\Delta^1$-cortienic acid have been described as putative inactive metabolites of the anti-inflammatory androstene derivatives of WO 97/42214 and Bodor U.S. Pat. No. 5,981,517. The '517 patent also describes the use of $\Delta^1$-cortienic acid as a competitor (with [3H]-triamcinolone acetonide as a tracer) for in vitro receptor binding studies of the androstene derivatives of that patent and notes similar studies of loteprednol etabonate. Druzgala et al., *J. Steroid Biochem. Molc. Biol., Vol.* 38, No. 2, pp. 149-154 (1991), reports earlier in vitro receptor binding studies of loteprednol etabonate and two putative metabolites, $\Delta^1$-cortienic acid and the corresponding 17α-ethyl carbonate, in a medium containing $10^{-5}$M cortienic acid as competitor, along with [3H]-triamcinolone acetonide as tracer. Druzgala et al. further note that loteprednol itself is intrinsically active, whereas the putative metabolites are indeed inactive. Neither these acids nor their esters have been previously suggested for use in pharmaceutical compositions for the treatment of inflammation because they are not themselves active as anti-inflammatory agents.

SUMMARY AND OBJECTS OF THE INVENTION

It has now been found that cortienic acid and related compounds enhance the topical or other local activity or duration of action of selected soft anti-inflammatory steroids.

Thus, in one aspect, the present invention provides a pharmaceutical composition of matter comprising:

(1) a combined synergistic anti-inflammatory effective amount of:

(a) a compound having the formula:

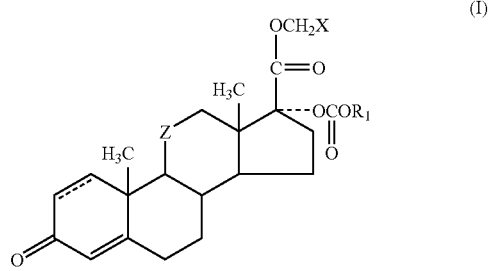

(I)

wherein:
R$_1$ is C$_1$-C$_7$ alkyl;
Z is carbonyl or β-hydroxymethylene;
X is Cl or F;
and the dotted line in ring A indicates that the 1,2-linkage is saturated or unsaturated;
and
(b) a compound having the formula:

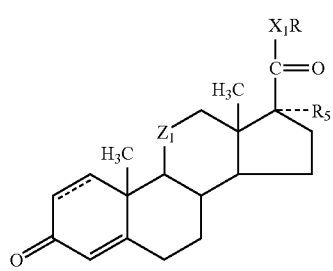

(II)

wherein:
R is H or C$_1$-C$_4$ alkyl;
Z$_1$ is carbonyl or β-hydroxymethylene;
X$_1$ is —O— or —S—;
R$_5$ is —OH, —OR$_6$, —OCOOR$_6$ or —OCOR$_7$ wherein R$_6$ is C$_1$-C$_4$ alkyl, and R$_7$ is C$_1$-C$_4$ alkyl, fluoromethyl or chloromethyl;
and the dotted line is defined as above;
with the proviso that when R is C$_1$-C$_4$ alkyl, then R$_5$ is —OH;
the amount of compound of formula (II) being sufficient to enhance the anti-inflammatory activity or duration of action, or both, of said compound of formula (I), and
(2) a non-toxic, pharmaceutically acceptable carrier therefor suitable for topical or other local application.

In another aspect, the invention provides a combination comprising (a) and (b) above, in a combined synergistic anti-inflammatory effective amount, the amount of (b) being sufficient to enhance the anti-inflammatory activity or duration of action, or both, of (a).

In another aspect, the invention provides the compositions and combinations as described above but with the proviso that [3H]-triamcinolone acetonide is not present in the composition or combination, or with the proviso that the composition or combination comprises (a) and (b) above as the only steroids in the composition; or with the proviso that the molar ratio of the compound of formula (II) to the compound of formula (I) is from about 5:1 to about 0.2:1 (preferably from about 0.5:1 to 1:1). The condition of one of these provisos is applicable when the compound of formula (II) has been previously employed in in vitro testing of the active compound, that is when the active compound is loteprednol etabonate and the compound of formula (II) is cortienic acid or Δ$^1$-cortienic acid. Of course, the compositions and combinations whose definitions include one of the provisos, but in which the active compound is other than loteprednol etabonate and/or the enhancer is other than cortienic acid or Δ$^1$-cortienic acid, include preferred aspects of the invention, in particular the provisos which specify the absence of the radiolabelled steroid and the use of the recited ratio.

In still a further aspect, the compositions described above are ophthalmic compositions and the carrier is a non-toxic, ophthalmically acceptable one.

In another aspect, the present invention provides a pharmaceutical composition of matter comprising:
(a) an anti-inflammatory effective amount of a compound having formula (I) as defined above;
(b) an amount of a compound of formula (II) as defined above sufficient to enhance the anti-inflammatory activity or duration of action, or both, of said compound of formula (I); and
(c) a non-toxic, pharmaceutically acceptable carrier suitable for topical or other local application;
with the optional provisos indicated hereinabove.

In yet another aspect, the invention provides a combination comprising:
(a) an anti-inflammatory effective amount of a compound having formula (I) as defined above; and
(b) an amount of a compound of formula (II) as defined above sufficient to enhance the anti-inflammatory activity or duration of action, or both, of said compound of formula (I).

In a further aspect of the invention, there is provided a composition as defined in the preceding paragraph in which the composition is ophthalmic and the carrier is a non-toxic, ophthalmically acceptable one.

In yet another aspect, the present invention provides a method for enhancing the anti-inflammatory activity or duration of action, or both, of a compound having formula (I) as defined above following topical or other local administration of said compound to a warm-blooded animal to alleviate a topical or other localized (e.g. ophthalmic) inflammatory response, said method comprising topically or otherwise locally (e.g. ophthalmically) co-administering said compound to said animal with a synergistically effective amount of a compound having formula (II) as defined above, the amount of the compound of formula (II) being sufficient to enhance the anti-inflammatory activity or duration of action, or both, of said compound of formula (I). Preferably, the compounds are co-administered in the form of one of the compositions of the invention defined above.

In still another aspect, the present invention provides a method for decreasing the in vivo transcortin binding of an anti-inflammatory steroid which binds to transcortin, and which is a compound having formula (I) as defined above, and for thus enhancing the anti-inflammatory activity or duration of action, or both, of said steroid following topical or other local administration of said steroid to a warm-blooded animal to alleviate a topical or other localized (e.g. ophthalmic) inflammatory response, said method comprising topically or otherwise locally (e.g. ophthalmically) co-administering said steroid to said animal with an amount of a compound having formula (II) above which is effective to decrease the in vivo transcortin binding of said steroid. Again, the compounds are preferably co-administered in the form of one of the compositions of the invention defined above.

In a further aspect, there is provided a method for enhancing the hydrolytic stability of a compound of formula (I) by combining therewith a carboxylic acid of formula (II), that is, a compound of formula (II) wherein X$_1$R is OH and the other structural variables are defined as above.

Thus, the present invention provides a new use of a compound of formula (II) in the preparation of a medicament for treatment of topical and other local inflammation, such as for treatment of ophthalmic inflammation; the compound of formula (II), while not itself having useful anti-inflammatory activity, is employed in accord with the present invention to enhance the activity of an anti-inflammatory steroid having transcortin binding activity, and having formula (I) above, by combining the compound of formula (II) with the active steroid of formula (I) in one of the compositions defined above.

DETAILED DESCRIPTION OF THE INVENTION

Throughout the instant specification and claims, the following definitions and general statements are applicable.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compositions described herein, i.e., the process or composition is limited to the specified steps or materials and those which do not materially affect the basic and novel characteristics of the invention. The basic and novel features herein are the provision of a combination of a compound of formula (I) with a compound of formula (II) which enhances the activity and/or duration of action of (I) for topical or other local application in the treatment of inflammation.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* $10^{th}$ Ed., McGraw Hill Companies Inc., New York (2001).

As used herein, "treating" means reducing, preventing, hindering or inhibiting the development of, controlling, alleviating and/or reversing the symptoms in the individual to which a combination or composition of the invention has been administered, as compared to the symptoms of an individual not being treated according to the invention. A practitioner will appreciate that the combinations, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The methods of the present invention are intended for use with any subject/patient that may experience the benefits of the methods of the invention. Thus, in accordance with the invention, the terms "subjects" as well as "patients," "individuals" and "warm-blooded animals" include humans as well as non-human subjects, particularly domesticated animals, particularly dogs, cats, horses and cows, as well as other farm animals, zoo animals and/or endangered species.

While not wishing to be bound by any particular theory, it is believed that the compounds of formula (II), while not themselves active as glucocorticoids, are able to enhance the glucocorticoid activity and/or duration of glucocorticoid action of the compounds of formulas (I) by competing with them in vivo for transcortin binding sites. The addition of the compound of formula (II) is believed to hinder efflux away from the site of local administration (which is also the site of action) of the active anti-inflammatory compound of formula (I) by competing with the active compound for various in vivo systems which transport away from the site. This is believed to thus contribute to an increase in the amount of free active compound available at the desired site of action/administration or to increase the time that the active compound remains at the site, or both.

With respect to the various groups encompassed by the generic terms used here and throughout the specification, the definitions and explanations given below are applicable.

$R_1$ is a straight or branched-chain alkyl radical having 1 to 7 carbon atoms, preferably 1 to 4 carbon atoms, such as methyl, ethyl, n-propyl, isopropyl, isobutyl and n-butyl.

Z is carbonyl or β-hydroxymethylene, preferably β-hydroxymethylene.

X is chloro or fluoro, preferably chloro.

R is H or straight or branched-chain alkyl having 1 to 4 carbon atoms; R is preferably H, methyl or ethyl.

$Z_1$ is carbonyl or β-hydroxymethylene, preferably β-hydroxymethylene.

$X_1$ is —O— or —S—, preferably —O—.

$R_5$ is —OH, —OR$_6$, —OCOOR$_6$ or —OCOR$_7$ wherein $R_6$ is straight or branched alkyl having 1 to 4 carbon atoms and $R_7$ is straight or branched alkyl having 1 to 4 carbon atoms, fluoromethyl or chloromethyl; preferably, $R_5$ is —OH.

In one embodiment of the invention, when $R_5$ in the compound of formula (II) is other than —OH, it may be selected to be identical to the 17α-substituent in the compound of formula (I) with which it is combined.

The dotted line in formulas (I) and (II) indicates that the A-ring can have the $\Delta^4$ or $\Delta^{1,4}$ configuration. In the case of the compounds of formula (II), there is at present a preference for the $\Delta^{1,4}$ configuration. In the case of compounds of formula (I), it is most preferred that the structural variables, including the presence or absence of a 1,2-double bond, correspond to those of loteprednol etabonate.

The compounds of formula (I) above are described in Bodor U.S. Pat. No. 4,996,335, incorporated by reference herein in its entirety and relied upon. Specific compounds of formula (I) disclosed in that patent and representative of compounds of formula (I) for use herein include the following:

1. chloromethyl 17α-ethoxycarbonyloxy-11β-hydroxyandrosta-1,4-dien-3-one-17β-carboxylate, also known as loteprednol etabonate or LE;
2. chloromethyl 11β-hydroxy-17α-methoxycarbonyloxyandrost-4-en-3-one-17β-carboxylate;
3. chloromethyl 17α-ethoxycarbonyloxy-11β-hydroxyandrost-4-en-3-one-17β-carboxylate;
4. chloromethyl 17α-butoxycarbonyloxy-11β-hydroxyandrost-4-en-3-one-17β-carboxylate;
5. chloromethyl 11β-hydroxy-17α-isopropoxycarbonyloxyandrost-4-en-3-one-17β-carboxylate;
6. chloromethyl 11β-hydroxy-17α-isopropoxycarbonyloxyandrosta-1,4-dien-3-one-17β-carboxylate;
7. chloromethyl 11β-hydroxy-17α-isobutoxycarbonyloxyandrost-4-en-3-one-17β-carboxylate;
8. chloromethyl 11β-hydroxy-17α-propoxycarbonyloxyandrost-4-en-3-one-17β-carboxylate;
9. fluoromethyl 11β-hydroxy-17α-isopropoxycarbonyloxyandrost-4-en-3-one-17β-carboxylate;
10. chloromethyl 11β-hydroxy-17α-n-propoxycarbonyloxyandrosta-1,4-dien-3-one-17β-carboxylate; and
11. chloromethyl 11β-hydroxy-17α-methoxycarbonyloxyandrosta-1,4-dien-3-one-17β-carboxylate.

As especially preferred compound of formula (I) for use in the present invention is chloromethyl 17α-ethoxycarbonyloxy-11β-hydroxyandrosta-1,4-dien-3-one-17β-carboxylate, or loteprednol etabonate. Loteprednol etabonate and other preferred compounds of formula (I) are those in which $R_1$ is methyl, ethyl, n-propyl, isopropyl, n-butyl or isobutyl, X is chloro, and Z is β-hydroxymethylene, most especially when the 1,2-linkage is unsaturated. These and other compounds of formula (I) can be prepared by methods described in the aforementioned '335 patent.

The compounds of formula (II) above have been variously described in the patent and non-patent literature as chemical intermediates to and/or inactive putative metabolites of active anti-inflammatory steroids. By "inactive" is meant that the compounds of formula (II) do not have significant glucocorticoid binding activity and do not elicit anti-inflammatory, anti-allergic or vasoconstriction activity. The preparation of cortienic acid, i.e. 11β, 17α-dihydroxyandrost-4-en-3-one-17β-carboxylic acid, from hydrocortisone by treatment with sodium metaperiodate is detailed in Example 1 of Bodor U.S. Pat. No. 4,996,335. Example 5B of that patent describes the analogous preparation of 17α-hydroxyandrost-4-en-3,11-dione-17β-carboxylic acid from cortisone; 11β,17α-dihydroxyandrosta-1,4-dien-3-one-17β-carboxylic acid from prednisolone; and 17α-hydroxyandrosta-1,4-dien-3,11-dione-17β-carboxylic acid from prednisone. The process of preparing the 17β-carboxylic acid from the corresponding 21-hydroxypregnenolones is generally described in column 10 of the '335 patent and in column 9 of Bodor U.S. Pat. No. 4,710,495. Example 10 of the '495 patent details a synthesis of 11β,17α-dihydroxyandrosta-1,4-dien-3-one-17β-carboxylic acid, i.e. $\Delta^1$-cortienic acid, from prednisolone. These patents describe the 17β-carboxylic acids of formula (II), i.e. the compounds in which —$X_1$R is —OH and $R_5$ is —OH, as chemical intermediates in the preparation of the compounds of formula (I) and other soft steroids. The thiocarboxylic acids (—$X_1$R═—SH) can be prepared analogously. Preferred 17β-carboxylic acids of formula (II) are cortienic acid and $\Delta^1$-cortienic acid.

The carboxylic acid esters of formula (II), i.e. the compounds in which —$X_1$R is —O—($C_1$-$C_4$ alkyl), can be prepared by combining 1 equivalent of the corresponding acid (—$X_1$R═—OH), i.e. cortienic acid or $\Delta^1$-cortienic acid, with 1.5 equivalents of anhydrous potassium carbonate in dimethylformamide (10 mL per gram of acid) or other suitable solvent, adding 3 equivalents of the selected $C_1$-$C_4$ alkyl iodide, such as methyl iodide or ethyl iodide, stirring the mixture for 2 hours at room temperature, then diluting the reaction mixture with water to precipitate the desired ester. The thiocarboxylic acid esters [—$X_1$R═—S—$C_1$-$C_4$ alkyl] can be prepared analogously starting from the thiocarboxylic acids. Preferred 17β-carboxylic acid esters of formula (II) are the methyl and ethyl esters of cortienic acid and the methyl and ethyl esters of $\Delta^1$-cortienic acid. These compounds are also referred to herein as cortienic acid methyl ester, cortienic acid ethyl ester, $\Delta^1$-cortienic acid methyl ester and $\Delta^1$-cortienic acid ethyl ester, respectively. Chemically, they can be named as methyl 11β,17α-dihydroxyandrost-4-en-3-one-17β-carboxylate; ethyl 11β,17α-dihydroxyandrost-4-en-3-one-17β-carboxylate; methyl 11β,17α-dihydroxyandrosta-1,4-dien-3-one-17β-carboxylate; and ethyl 11β,17α-dihydroxyandrosta-1,4-dien-3-one-17β-carboxylate, respectively. Example 5 of Bodor U.S. Pat. No. 4,710,495, details an alternate process for making these esters; it specifically describes methyl 11β,17α-dihydroxyandrost-4-en-3-one-17β-carboxylate, i.e. the 17β-carboxylic acid methyl ester of cortienic acid, also referred to herein as cortienic acid methyl ester.

When —$X_1$R is —OH or —SH in formula (II), $R_5$ can be not only —OH as discussed above, but can alternatively be a carbonate (—OCOOR$_6$), ether (—OR$_6$) or ester (—OCOR$_7$) grouping. The preparation of the formula (II) 17β-carboxylic acid 17α-carbonates/17β-thiocarboxylic acid 17α-carbonates ($X_1$R═SH) is described in the aforementioned Bodor U.S. Pat. No. 4,996,335 and proceeds by reacting the corresponding acid or thio acid (R═H) of formula (II) with $R_6$OCOCl or $R_6$OCOBr (formed by reacting $R_6$OH with COCl$_2$ or COBr$_2$, wherein $R_6$ is defined as above), under anhydrous conditions in an appropriate inert organic solvent in the presence of a suitable acid acceptor. Examples 2 (first paragraph), 6A, 6B, 6C, 19 and 20 of the '335 patent describe preparation of compounds of this type. Representative specific compounds described therein which can be used in the present invention include:

1. 11β-hydroxy-17α-methoxycarbonyloxyandrost-4-en-3-one-17β-carboxylic acid;
2. 17α-ethoxycarbonyloxy-11β-hydroxyandrost-4-en-3-one-17β-carboxylic acid;
3. 17α-butoxycarbonyloxy-11β-hydroxyandrost-4-en-3-one-17β-carboxylic acid;
4. 11β-hydroxy-17α-isopropoxycarbonyloxyandrost-4-en-3-one-17β-carboxylic acid;
5. 11β-hydroxy-17α-isobutoxycarbonyloxyandrost-4-en-3-one-17β-carboxylic acid;
6. 11β-hydroxy-17α-propoxycarbonyloxyandrost-4-en-3-one-17β-carboxylic acid;
7. 11β-hydroxy-17α-methoxycarbonyloxyandrosta-1,4-dien-3-one-17β-carboxylic acid; and
8. 17α-ethoxycarbonyloxy-11β-hydroxyandrost-1,4-dien-3-one-17β-carboxylic acid.

Other specific compounds described in the '335 patent but not named therein which can be used in the present invention are identified in Example 6B of the patent as compound nos. 6B-1, 6B-2, and 6B-10 and can be named as 17α-ethoxycarbonyloxyandrost-4-ene-3,11-dione-17β-carboxylic acid; 17α-methoxycarbonyloxyandrost-4-ene-3,11-dione-17β-carboxylic acid; and 17α-ethoxycarbonyloxyandrosta-1,4-diene-3,11-dione-17β-carboxylic acid, respectively.

The preparation of the formula (II)17β-carboxylic acid 17α-ethers/17β-thiocarboxylic acid 17α-ethers (X$_1$R=OH/SH; R$_5$=OR$_6$) is described in the aforementioned Bodor U.S. Pat. No. 4,710,495. Typically, cortienic acid or Δ$^1$-cortienic acid or the corresponding X$_1$=S acid is reacted with R$_6$I and KOH under anhydrous conditions, in an inert organic solvent, preferably in the presence of a suitable acid acceptor, to afford the corresponding 17α-alkoxy 17β-carboxylic acid ester of the formula

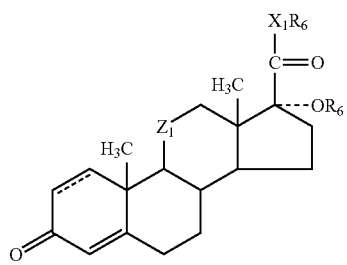

which is thereafter converted to the desired 17β-carboxylic acid 17α-ethers of the formula

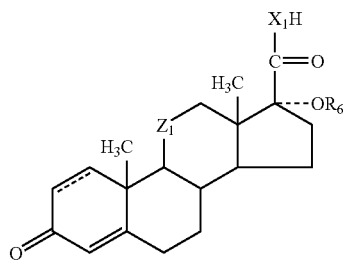

by reaction with KOH, under anhydrous conditions, in an appropriate inert organic solvent. Representative specific compounds described therein which are suitable for use herein include 11β-hydroxy-17α-methoxyandrost-4-en-3-one-17β-carboxylic acid (Examples 3 and 23); 17α-ethoxy-11β-hydroxyandrost-4-en-3-one-17β-carboxylic acid (Examples 8 and 30); 11β-hydroxy-17α-propoxyandrost-4-en-3-one-17β-carboxylic acid (Examples 8 and 30); 17α-butoxy-11β-hydroxyandrost-4-en-3-one-17β-carboxylic acid (Examples 8 and 30); 11β-hydroxy-17α-methoxyandrosta-1,4-dien-3-one-17β-carboxylic acid (Example 12); and 11β-hydroxy-17α-propoxyandrosta-1,4-dien-3-one-17β-carboxylic acid (Example 12). Another compound of this type suitable for use herein which can be prepared in analogous fashion is 17α-ethoxy-11β-hydroxyandrost-1,4-dien-3-one-17β-carboxylic acid.

The formula (II) 17β-carboxylic acid 17α-esters and 17β-thiocarboxylic acid 17α-esters (X$_1$R=OH/SH; R$_5$=OCOR$_7$) can be prepared by reacting the corresponding acid or thio acid (R=H) of formula (II) with R$_7$COCl or R$_7$COBr. For example, 11β,17α-dihydroxyandrosta-1,4-dien-3-one-17β-carboxylic acid (Δ$^1$-cortienic acid; 3.12 g, 9.0 mmol) is dissolved in a solution of sodium bicarbonate (7.56 g, 90 mmol) in water (100 mL). Methylene chloride (100 mL) is added, followed by tetrabutylammonium hydrogensulfate (1.0 g). The mixture is stirred vigorously and acetyl chloride (17 mmol) in methylene chloride (10 mL) is added dropwise over a period of 5 minutes. Stirring is continued for approximately 5 hours, then the organic phase is separated and washed successively with 5% aqueous sodium bicarbonate solution, water, and saturated aqueous sodium thiosulfate solution. The organic solution is dried over sodium sulfate and concentrated in vacuo. The resulting crude product, 17α-acetoxy-11β-hydroxyandrosta-1,4-dien-3-one-17β-carboxylic acid, is purified by chromatography. Substantial repetition of this procedure utilizing an equivalent quantity of propionyl chloride or butyryl chloride in place of the acetyl chloride affords 11β-hydroxy-17α-propionyloxyandrosta-1,4-dien-3-one-17β-carboxylic acid and 17α-butyryloxy-11β-hydroxyandrosta-1,4-dien-3-one-17β-carboxylic acid, respectively. Similarly, repetition of this procedure, but utilizing an equivalent quantity of 11β,17α-dihydroxyandrost-4-en-3-one-17β-carboxylic acid together with acetyl chloride, propionyl chloride or butyryl chloride as the reactants affords, respectively, 17α-acetoxy-11β-hydroxyandrost-4-en-3-one-17β-carboxylic acid, 11-hydroxy-17α-propionyloxyandrost-1,4-dien-3-one-17β-carboxylic acid and 17α-butyryloxy-11β-hydroxyandrost-4-en-3-one-17β-carboxylate.

At the present time, compounds of formula (II) in which R$_5$ is —OH are of particular interest, especially those having the formula:

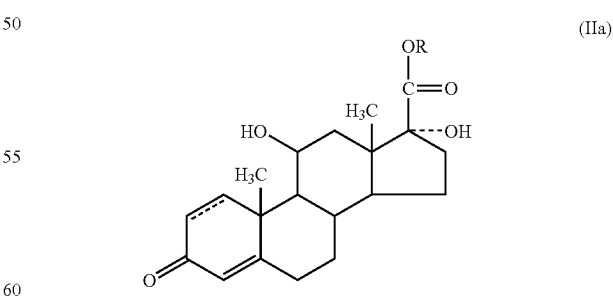

wherein R is H or C$_1$-C$_4$ alkyl and the dotted line indicates that the 1,2-linkage is saturated or unsaturated, most especially when R is H, methyl or ethyl.

In the compositions and methods of the present invention, the enhancing agent of formula (II) and compound of formula (I) are generally used in a molar ratio of from about 5:1 to about 0.2:1 (preferably from about 0.5:1 to about 1:1), that is, from about 0.2 to about 5 moles (preferably from about 0.5 to about 1 mole) of the formula (II) compound for each mole of compound of formula (I). In situations in which the molecular weight of the formula (II) compound is similar to that of the selected compound of formula (I), a weight/weight ratio of from about 5:1 to about 0.2:1 (preferably 0.5:1 to 1:1, approximately) will closely approximate the about 5:1 to about 0.2:1 (preferably about 0.5:1 to about 1:1) molar ratio and can be used instead for ease in formulating pharmaceutical formulations. Indeed, even when the molecular weight of the compound of formula (I) is 10-20% greater than that of the formula (II) compound, the about 5:1 to about 0.2:1 (II):(I) (preferably about 0.5:1 to about 1:1) weight ratio can be conveniently employed.

The present invention also provides a method for enhancing the hydrolytic stability of a compound of formula (I) by combining therewith a carboxylic acid of formula (II), that is, a compound of formula (II) wherein $X_1R$ is OH and the other structural variables are defined as above, in an amount sufficient to enhance the hydrolytic stability of the compound of formula (I). Of particular interest in this regard are the compounds of formula (IIa) in which R is H, i.e. cortienic acid and $\Delta^1$-cortienic acid. These acids of formula (II), especially the two acids of formula (IIa) named above, when in solution produce an acidic environment which enhances the hydrolytic stability of the compound of formula (I), for example, of loteprednol etabonate. Generally speaking, the same amounts described herein as sufficient to enhance the anti-inflammatory activity and/or duration of action of the compound of formula (I) are also sufficient to enhance its hydrolytic stability.

The compounds of formulas (I) and (II) can be combined with suitable non-toxic pharmaceutically acceptable carriers to provide pharmaceutical compositions for use in the treatment of topical or other localized inflammation. Obviously, in view of their lack of systemic activity, compositions containing the compounds of formula (I) are not intended for treatment of conditions where systemic adrenocortical therapy is indicated, e.g., adrenocortical insufficiency. As examples of inflammatory conditions which can be treated with pharmaceutical compositions containing the combination of a compound of formula (I) and a compound of formula (II) and one or more pharmaceutical carriers, the following can be mentioned: dermatological disorders such as atopic dermatitis, acne, psoriasis or contact dermatitis; allergic states such as bronchial asthma; ophthalmic and otic diseases involving acute and chronic allergic and inflammatory reactions (for example, ophthalmic inflammatory conditions such as blepharitis, conjunctivitis, episcleritis, scleritis, keratitis, anterior uveitis and sympathetic ophthalmia, and ear inflammations of the outer and middle ear as well as inflammation of the inner ear, for example Meniere's Disease, injected or instilled into the inner ear through the ear drum analogous to the current use of dexamethasone); respiratory diseases; inflammations of the mouth, gums and/or throat, such as gingivitis or oral aphtha; inflammations of the nasal mucosa, for example, those caused by allergies; inflammations of the upper and lower intestines, such as Crohn's disease and ulcerative colitis; inflammations associated with arthritis; and anorectal inflammation, pruritus and pain associated with hemorrhoids, proctitis, cryptitis, fissures, postoperative pain and pruritus ani. Such compositions may also be applied locally as a prophylactic measure against the inflammation and tissue rejection which arise in connection with transplants.

Obviously, the choice of carrier(s) and dosage forms will vary with the particular condition for which the composition is to be administered.

Examples of various types of preparations for topical/local administration include ointments, gels, lotions, creams, powders, drops (e.g., eye or ear or nose drops), sprays (e.g., for the nose or throat), suppositories, retention enemas, chewable or suckable tablets or pellets (e.g., for the treatment of aphthous ulcers) aerosols, tablets and capsules.

Ointments and creams or gels may, for example, be formulated with an aqueous or oily base with the addition of suitable thickening and/or gelling agents and/or glycols. Such base may thus, for example, include water and/or an oil such as liquid paraffin or a vegetable oil such as arachis oil or castor oil, or a glycolic solvent such as propylene glycol or 1,3-butanediol. Thickening agents which may be used according to the nature of the base include soft paraffin, aluminum stearate, cetostearyl alcohol, polyethylene glycols, woolfat, hydrogenated lanolin and beeswax and/or glyceryl monostearate and/or non-ionic emulsifying agents.

The solubility of the steroids in the ointment or cream may be enhanced by incorporation of an aromatic alcohol such as benzyl alcohol, phenylethyl alcohol or phenoxyethyl alcohol.

Lotions may be formulated with an aqueous or oily base and will in general also include one or more of the following, namely, emulsifying agents, dispersing agents, suspending agents, thickening agents, solvents, coloring agents and perfumes.

Powders may be formed with the aid of any suitable powder base e.g., talc, lactose or starch.

Drops may be formulated with an aqueous base also comprising one or more dispersing agents, suspending agents or solubilizing agents, etc.

Spray compositions may, for example, be formulated as aerosols with the use of a suitable propellant, e.g., dichlorodifluoromethane or trichlorofluoromethane.

Nebulized or powdered formulations may be prepared for oral inhalation in the treatment of asthma, as is well-known in the art.

Solutions and suspensions may be prepared for oral or rectal administration for use in the treatment of inflammations of the intestines, for example, as described in more detail in the examples hereinafter. Moreover, tablets, capsules and other oral dosage forms may be used, for example, in the treatment of Crohn's disease, provided that they are formulated for delayed release (such as three hours after administration) to protect the compounds of formulas (I) and (II) from gastric juice and to thus allow them to reach the target site, such as the duodenum, before dissolving.

Parenteral/injectable formulations may be prepared for direct injection into the joints in the treatment of arthritis in accord with methods well-known to those skilled in the art of parenteral formulations.

The amount of active ingredient and enhancer in the compositions according to the invention will vary with the precise compounds used, the type of formulation prepared and the particular condition for which the composition is to be administered. The formulation will generally contain from about 0.0001 to about 5.0% by weight of the compound of formula (I). Topical preparations will generally contain 0.0001 to 2.5%, preferably 0.01 to 0.5% of active compound, and will be administered once daily, or as needed. The identity and amount of active compound will determine the amount of formula (II) compound utilized therewith, in keeping with the desired molar or weight ratios discussed above. Also, generally speaking, the compounds of formulas (I) and (II) can be incorporated into topical and other local compositions formulated substantially as are such presently available types of compositions containing known glucocorticosteroids, with the amount of compound of formula (I) varying according to its potency.

The compositions of the invention may be formulated to include other active compounds known to be useful in combination with anti-inflammatory steroids, for example, antifungal, antibacterial, antibiotic and local anaesthetic agents, for example, clotrimazole, clioquinol (iodochlorhydroxyquin), iodoquinol, polymyxin B sulfate, neomycin sulfate, tobramycin, sulfacetamide sodium, gentamicin, thonzonium bromide, colistin sulfate and pramoxine hydrochloride. The steroids of formulas (I) and (II) may be combined with more than one of these additional active agents when appropriate, for example, with a combination of polymyxin B sulfate and neomycin sulfate.

The anti-inflammatory activity of the compounds of formula (I) is well-known from the aforementioned Bodor U.S. Pat. No. 4,996,335 and the scientific literature; as noted earlier, one of these compounds, loteprednol etabonate, is currently marketed in the United States for ophthalmic administration as an anti-inflammatory agent. The marketed 0.2% sterile ophthalmic suspension is indicated for the temporary relief of signs and symptoms of seasonal allergic conjunctivitis while the marketed 0.5% sterile ophthalmic suspension is indicated for the treatment of steroid-responsive inflammatory conditions of the palpebral and bulbar conjunctiva, cornea and anterior segment of the globe such as allergic conjunctivitis, acne rosacea, superficial punctate keratitis, herpes zoster keratitis, iritis, cyclitis, selected infective conjunctivitides, to reduce edema and inflammation. Other formulations for local administration for a variety of conditions are in clinical trials.

The combinations of the present invention have undergone human vasoconstriction, or blanching, testing. Such testing gives a reliable indication of local anti-inflammatory/glucocorticoid activity. In the present case, it has been used to show that representative enhancing agents of formula (II) are inactive alone, that a representative compound of formula (I) is active alone, and that administering a compound of formula (II) with a compound of formula (I) enhances the anti-inflammatory activity or duration of action or both of the representative formula (I) compound.

Human Vasoconstriction Testing

Test compounds at varying mM concentrations as noted below were dissolved in ethanol/propylene glycol (9/1) solution, and 20 μL of the mixtures were applied to filter paper discs, 0.7 cm in diameter. After ethanol evaporation, each disc was attached to waterproof adhesive tape, then applied to the forearm of a human volunteer and left in place for 4 hours. Groups of 8 forearms were tested at each concentration. The intensity of vasoconstriction was judged at 2, 4, 6, 8, 10, 12, 18, 24 and 36 hours after removal of the discs.

The grading scale for the vasoconstriction activity was as follows: 0, normal skin; 1, slight pallor of indistinct outline; 2, pallor with at least two corners outlined; 3, even pallor with a clear outline of the application sites; 4, very intense pallor. The scores were totaled at each concentration at each time after removal to give a total score at each time interval and an overall total for each concentration. The higher the total score, the greater the blanching or anti-inflammatory effect.

Tested in this manner were loteprednol etabonate, $\Delta^1$-cortienic acid, the methyl ester of $\Delta^1$-cortienic acid, a combination of loteprednol etabonate plus $\Delta^1$-cortienic acid, and a combination of loteprednol etabonate plus the methyl ester of $\Delta^1$-cortienic acid. The structures of the test compounds are shown below:

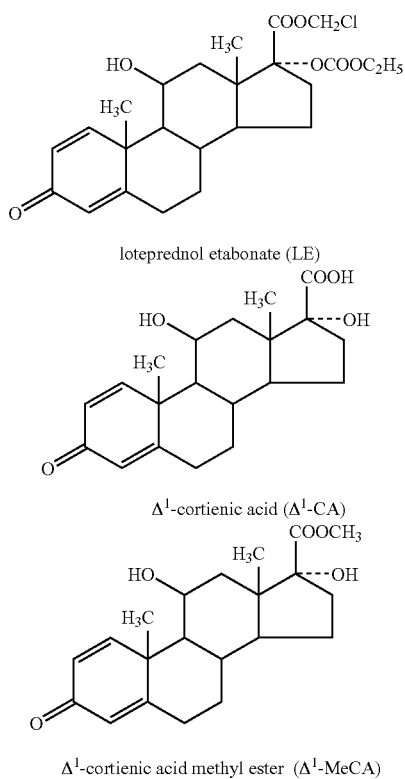

loteprednol etabonate (LE)

$\Delta^1$-cortienic acid ($\Delta^1$-CA)

$\Delta^1$-cortienic acid methyl ester ($\Delta^1$-MeCA)

The results were as follows, where AUC was estimated as the sum of the individual scores through 36 hours.

Loteprednol Etabonate

| Concentration | | |
|---|---|---|
| mM | % by weight | AUC |
| 0.1 | 0.0047% | 9 |
| 0.5 | 0.023% | 39 |
| 1 | 0.047% | 90 |
| 5 | 0.23% | 117 |
| 10 | 0.47% | 122 |

$\Delta^1$-Cortienic Acid

| Concentration | | |
|---|---|---|
| mM | % by weight | AUC |
| 0.5 | 0.017% | 0 |
| 2.5 | 0.09% | 0 |
| 5 | 0.17% | 0 |
| 25 | 0.87% | 0 |
| 50 | 1.73% | 0 |

$\Delta^1$-Cortienic Acid Methyl Ester

| Concentration | | AUC |
|---|---|---|
| mM | % by weight | |
| 0.5 | 0.018% | 0 |
| 2.5 | 0.09% | 0 |
| 5 | 0.18% | 0 |
| 25 | 0.90% | 0 |
| 50 | 1.80% | 0 |

Loteprednol Etabonate+$\Delta^1$-Cortienic Acid

| Concentration (mM) | | AUC |
|---|---|---|
| LE | $\Delta^1$-CA | |
| 0.1 | 0.5 | 36 |
| 0.5 | 2.5 | 78 |
| 1 | 5 | 112 |
| 5 | 25 | 127 |
| 10 | 50 | 128 |

Loteprednol Etabonate+$\Delta^1$-Cortienic Acid Methyl Ester

| Concentration (mM) | | AUC |
|---|---|---|
| LE | $\Delta^1$-MeCA | |
| 0.5 | 0.5 | 40 |
| 2.5 | 2.5 | 91 |
| 5 | 5 | 117 |
| 25 | 25 | 128 |
| 50 | 50 | 132 |

The results indicate that neither $\Delta^1$-cortienic acid nor $\Delta^1$-cortienic acid mehtyl ester had any vasoconstriction activity when tested alone. Loteprednol etabonate alone exhibited significant activity, as would be expected. Surprisingly, $\Delta^1$-cortienic acid and $\Delta^1$-cortienic acid methyl ester each significantly enhanced the vasoconstrictor activity of loteprednol etabonate, especially at the lower concentrations tested. A 1:5 molar ratio of loteprednol etabonate: $\Delta^1$-cortienic acid or its methyl ester was used throughout.

It was also found that the activity of loteprednol etabonate alone began to decrease between 12 and 18 hours after removal of the disc, a decrease which was even more apparent at the 24 hour interval. $\Delta^1$-Cortienic acid and $\Delta^1$-cortienic methyl ester were each able to extend the time period during which loteprednol etabonate displayed significant activity, to 24 hours or more at some tested concentrations.

This testing clearly showed the synergistic effect which $\Delta^1$-cortienic acid and its methyl ester each exert on the anti-inflammatory action of loteprednol etabonate as well as on its duration of action.

Further Human Vasoconstriction Testing

Objective

The objective of this study is to evaluate the effect of $\Delta^1$-cortienic acid ($\Delta^1$-CA) and the methyl ester of $\Delta^1$-cortienic acid ($\Delta^1$-MeCA) on the vasoconstriction effect of loteprednol etabonate (LE) and betamethasone 17-valerate (BEM-17V). The structures of LE, $\Delta^1$-CA and $\Delta^1$-MeCA are given above.

BEM-17V has the structure:

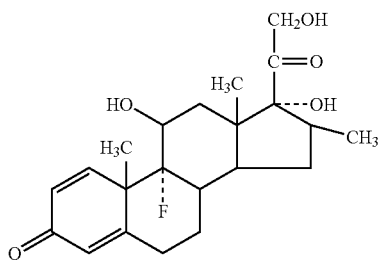

and was used for comparison purposes.

Methodology

LE (0.2 mM), BEM-17V (0.2 mM), $\Delta^1$-CA (0-1 mM) and $\Delta^1$-MeCA (0-1 mM) solutions were made by dissolving the compounds in a vehicle containing absolute ethanol and propylene glycol (9:1). The resultant LE and BEM-17V solutions were then mixed (1:1) with vehicle only, or with the $\Delta^1$-CA or $\Delta^1$-MeCA solutions, so that LE solutions (0.1 mM) and BEM-17V solutions (0.1 mM) containing various concentrations of $\Delta^1$-CA (0 to 0.5 mM) or $\Delta^1$-MeCA (0 to 0.5 mM) were obtained. The resultant mixtures (20 μl) were loaded onto circular patches (6.5 mm diameter) that were attached to a water impervious adhesive film (3M). After the evaporation of ethanol, the patches and film were applied to the forearms of human volunteers for 4 hours. Subsequently, the vasoconstriction reaction was judged by the appearance of pallor at various time intervals after the removal of the patches (2, 4, 6, 8, 10, 12, 18, 20 and 24 hours after removal and also 36 hours after removal in the case of BEM-VAL). The grading scale was as follows: 0, normal skin; 1, slight pallor; 2, pallor with at least two corners outlined; 3, even pallor with a clear outline of the application sites; 4, very intense pallor. Due to the response variations among the volunteers, control tests (0 mM $\Delta^1$-CA and $\Delta^1$-MeCA) were performed on each tested arm at the same time, and the total scores of the tests were taken at each time period and compared. As before, an overall total for each concentration was then obtained. The results were as follows, where AUC was estimated as the sum of the individual scores through 24 hours.

Results and Discussion

Loteprednol Etabonate+Δ¹-Cortienic Acid

| Concentration (mM) | | |
|---|---|---|
| LE | Δ¹-CA | AUC |
| 0.1 | 0 | 99 |
| 0.1 | 0.1 | 122 |
| 0.1 | 0.2 | 121 |
| 0.1 | 0.3 | 123 |
| 0.1 | 0.4 | 125 |
| 0.1 | 0.5 | 116 |

Loteprednol Etabonate+Δ¹-Cortienic Acid Methyl Ester

| Concentration (mM) | | |
|---|---|---|
| LE | Δ¹-MeCA | AUC |
| 0.1 | 0 | 114 |
| 0.1 | 0.1 | 121 |
| 0.1 | 0.2 | 123 |
| 0.1 | 0.3 | 127 |
| 0.1 | 0.4 | 126 |
| 0.1 | 0.5 | 122 |

Betamethasone Valerate+Δ¹-Cortienic Acid

| Concentration (mM) | | |
|---|---|---|
| BEM-17V | Δ¹-CA | AUC |
| 0.1 | 0 | 107 |
| 0.1 | 0.1 | 107 |
| 0.1 | 0.2 | 107 |
| 0.1 | 0.3 | 107 |
| 0.1 | 0.4 | 107 |
| 0.1 | 0.5 | 107 |

Betamethasone Valerate+Δ¹-Cortienic Acid Methyl Ester

| Concentration (mM) | | |
|---|---|---|
| BEM-17V | Δ¹-MeCA | AUC |
| 0.1 | 0 | 112 |
| 0.1 | 0.1 | 112 |
| 0.1 | 0.2 | 112 |
| 0.1 | 0.3 | 112 |
| 0.1 | 0.4 | 112 |
| 0.1 | 0.5 | 112 |

Human vasoconstriction tests have been used to evaluate the percutaneous absorption, activity and bioavailability of glucocorticoids. The vasoconstriction activity of LE, and the effect of Δ¹-CA and Δ¹-MeCA on the activity of LE have been studied and reported hereinabove. In the present study, the effects of Δ¹-CA and Δ¹-MeCA on the activities of LE and BEM-17V were compared at varying molar ratios of drug to Δ¹-CA and Δ¹-MeCA. The results shown in the first two tables indicate that, as in the previous studies, Δ¹-CA and Δ¹-MeCA both increased the vasoconstriction activity of LE. Ratios of 1:1 of LE: Δ¹-CA and Δ¹-MeCA gave very similar results to those obtained for 1:2, 1:3, 1:4 and 1:5 ratios, with 1:5 ratios showing slightly less activity. All of these ratios showed synergistic results. In other words, molar ratios of (II) to (I) of from 5:1 to 1:1 showed synergism. Ratios of about 1:1 appear most useful; increasing the ratio of (II) to (I) to 2:1 or even 5:1 does not give better results. In the case of BEM-17V, no activity-increasing effect of Δ¹-CA and Δ¹-MeCA was observed, as shown in the third and fourth tables above.

The following Examples illustrate numerous formulations suitable for administering the combinations of a compound of formula (I) and a compound of formula (II) to treat various kinds of local inflammatory conditions. These formulations are merely illustrative and not limitative of the remainder of the specification and claims in any way whatsoever.

In these Examples, percentages are by weight unless otherwise noted.

EXAMPLE 1

A nasal suspension is prepared having the following composition:

| NASAL SUSPENSION | |
|---|---|
| Loteprednol etabonate (LE) | 0.5 to 1.0 g |
| Δ¹-Cortienic acid | 2.5 to 5.0 g (in 5:1 ratio to LE) |
| Concentrated glycerin | 2.6 g |
| Polysorbate 80 | 0.2 g |
| Microcrystalline cellulose carmellose sodium | 2.0 to 3.0 g |
| Citric acid | q.s. |
| Benzalkonium chloride | 0.005 g |
| Purified water q.s. | 100 g (pH 5.5) |

The suspension can be prepared in accord with the procedure described in Doi U.S. Pat. No. 6,368,616 B1 of Apr. 9, 2002, incorporated by reference herein in its entirety and relied upon, except for the addition of Δ¹-cortienic acid, which can occur at the same time as the addition of loteprednol etabonate.

Alternatively, from 0.5 to 1.0 g of Δ¹-cortienic acid may be used instead of the 2.5 to 5.0 g amount listed above.

EXAMPLE 2

A nasal suspension is prepared having the following composition:

| NASAL SUSPENSION | |
|---|---|
| Loteprednol etabonate | 0.5 g |
| Δ¹-Cortienic acid methyl ester | 0.25 to 2.5 g |
| Propylene glycol | 2.0 g |
| Polyoxyethylene hydrogenated castor oil 60 | 0.2 g |
| Microcrystalline cellulose carmellose sodium | 3.0 g |
| Phosphoric acid | q.s. |
| Benzethonium chloride | 0.005 g |
| Purified water q.s. | 100 g (pH 5.5) |

The suspension can be prepared in accord with the procedure of the aforementioned '616 patent, except for the addition of $\Delta^1$-cortienic acid methyl ester, which can occur at the same time as the addition of loteprednol etabonate.

The foregoing nasal formulations can be modified as described in the '616 patent.

The following formulations can be prepared using routine production procedures for formulations of these types.

EXAMPLE 3

An eye drop suspension is prepared having the following composition:

| EYE DROP SUSPENSION | |
|---|---|
| Loteprednol etabonate | 0.5 g |
| $\Delta^1$-Cortienic acid methyl ester | 0.25 to 2.0 g |
| ε-Aminocaproic acid | 0.1 g |
| Tyloxapol | 0.3 g |
| Polyvinylpyrrolidone (intrinsic viscosity = 30) | 0.6 g |
| Sodium edetate | 0.01 g |
| Benzalkonium chloride (10 w/v %) | 0.05 mL |
| Hydrochloric acid | q.s. |
| Sterilized pure water | q.s. 100 mL |
| pH | 5.53 |

0.05 to 0.1 mL of this suspension can be distilled into the eye 3 to 10 times daily.

This suspension formulation can be modified as described in Inada et al U.S. Pat. No. 5,916,550, of Jun. 29, 1999, incorporated by reference herein in its entirety and relied upon, except for the addition of $\Delta^1$-cortienic acid methyl ester at the time of loteprednol etabonate incorporation, to provide other aqueous suspensions for use in the eye or nose which do not undergo pH depression even after prolonged storage.

EXAMPLE 4

An ointment is prepared having the following composition:

| OINTMENT | |
|---|---|
| Compound of formula (I) e.g. loteprednol etabonate | 0.10% w/w |
| Compound of formula (II), e.g. $\Delta^1$-cortienic acid methyl ester | 0.10 to 0.40% w/w |
| Liquid paraffin | 10.0% ww |
| White soft paraffin | 89.5% w/w |

EXAMPLE 5

Anaphthous ulcer pellet is prepared having the following composition:

| APHTHOUS ULCER PELLET | |
|---|---|
| Compound of formula (I), e.g. loteprednol etabonate | 0.20 mg |
| Compound of formula (II), e.g. $\Delta^1$-cortienic acid | 0.20 to 0.80 mg |
| Lactose | 69.0 mg |
| Acacia | 3.00 mg |
| Magnesium stearate | 0.75 mg |

EXAMPLE 6

A retention enema is prepared having the following composition:

| RETENTION ENEMA | |
|---|---|
| Compound of formula (I), e.g. loteprednol etabonate | 0.01% w/v |
| Compound of formula (II), e.g. $\Delta^1$-cortienic acid methyl ester | 0.01% to 0.03% w/v |
| Tween 80 | 0.05% w/v |
| Ethanol | 0.015% w/v |
| Propylparaben | 0.02% w/v |
| Methylparaben | 0.08% w/v |
| Distilled water | q.s. 100 volumes |

EXAMPLE 7

Eye drops are prepared having the following composition:

| EYE DROPS | |
|---|---|
| Compound of formula (I), e.g. loteprednol etabonate | 0.2% w/v |
| Compound of formula (II), e.g. $\Delta^1$-cortienic acid | 0.20 to 0.80% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

EXAMPLE 8

A dermal ointment is prepared having the following composition:

| DERMAL OINTMENT | |
|---|---|
| Compound of formula (I), e.g. loteprednol etabonate | 0.2% w/w |
| Compound of formula (II), e.g. $\Delta^1$-cortienic acid | 0.1 to 1.0% w/w |
| Liquid Paraffin | 10.0% w/w |
| White soft paraffin | 88.8% w/w |

EXAMPLE 9

Anaphthous ulcer pellet is prepared having the following composition:

| APHTHOUS ULCER PELLET | |
|---|---|
| Compound of formula (I), e.g. loteprednol etabonate | 0.15 mg |
| Compound of formula (II), e.g. $\Delta^1$-cortienic acid methyl ester | 0.10 to 0.45 mg |
| Lactose | 60.25 mg |
| Acacia | 3.0 mg |
| Magnesium sterate | 0.75 mg |

EXAMPLE 10

A retention enema is prepared having the following composition:

| RETENTION ENEMA | |
|---|---|
| Compound of formula (I), e.g. loteprednol etabonate | 0.005% w/v |
| Compound of formula (II), e.g. $\Delta^1$-cortienic acid | 0.003 to 0.025% w/v |
| Tween 80 | 0.05% w/v |
| Ethanol | 0.015% w/v |
| Propylparaben | 0.02% w/v |
| Methylparaben | 0.08% w/v |
| Distilled water | q.s. 100 volumes |

EXAMPLE 11

Eye drops are prepared having the following composition:

| EYE DROPS | |
|---|---|
| Compound of formula (I), e.g. loteprednol etabonate | 0.1% w/v |
| Compound of formula (II), e.g. $\Delta^1$-cortienic acid methyl ester | 0.1 to 0.5% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

EXAMPLE 12

Eye drops are prepared having the following composition:

| EYE DROPS | |
|---|---|
| Compound of formula (I), e.g. loteprednol etabonate | 0.5% w/v |
| Compound of formula (II), e.g. $\Delta^1$-cortienic acid | 0.25 to 1.5% w/v |
| Povidone | 0.6% w/v |
| Benzalkonium chloride | 0.02% w/v |
| Sodium edetate U.S.P. | 0.10% w/v |
| Glycerin U.S.P. | 2.5% w/v |
| Tyloxapol U.S.P. | 3.0% w/v |
| Sodium chloride | 0.3% w/v |
| Sodium γ-aminobutyrate | 1.0% w/v |
| Sterile distilled water | q.s. 100 volumes |

The ingredients listed above are combined, then the pH is checked and, if necessary, adjusted to 5.0-5.5 by basifying with sodium hydroxide or acidifying with hydrochloric acid.

Yet other compositions of the invention can be conveniently formulated using known techniques.

Thus, for example, an inhalation formulation suitable for use in the treatment of asthma can be prepared as a metered-dose aerosol unit containing a representative compound of formula (I) such as loteprednol etabonate and a representative compound of formula (II) such as cortienic acid, cortienic acid methyl ester, $\Delta^1$-cortienic acid or $\Delta^1$-cortienic methyl ester, according to procedures well-known to those skilled in the art of pharmaceutical formulations. Such an aerosol unit may contain a microcrystalline suspension of loteprednol etabonate and one of the aforementioned compounds of formula (II) in a I:(II) weight ratio of from 0.5:1 to 1:3 in suitable propellants (e.g. trichlorofluoromethane and dichlorodifluoromethane and dichlorotetrafluoroethane), with oleic acid, sorbitan trioleate or other suitable dispersing agent. Each unit typically contains 1-10 milligrams of the aforesaid loteprednol etabonate, approximately 5-50 micrograms of which are released at each actuation.

Another example of a pharmaceutical composition according to the invention is a foam suitable for treatment of a wide variety of inflammatory anorectal disorders, to be applied anally or perianally, comprising 0.1% or 0.5% of a compound of formula (I) such as loteprednol etabonate and 0.2% or 1.0%, respectively, of $\Delta^1$-cortienic acid or its methyl ester, and 1% of a local anaesthetic such as pramoxine hydrochloride, in a mucoadhesive foam base of propylene glycol, ethoxylated stearyl alcohol, polyoxyethylene-10-stearyl ether, cetyl alcohol, methyl paraben, propyl paraben, triethanolamine, and water, with inert propellants. Alternatively, 0.2% or 1.0% of $\Delta^1$-cortienic acid or its methyl ester may be employed (in a 1:1 ratio of (I):(II)).

Yet another pharmaceutical formulation according to the invention is a solution or suspension suitable for use as a retention enema, a single dose of which typically contains 40-80 milligrams of a compound of formula (I) such as loteprednol etabonate and from ½ to 5 times that amount of a compound of formula (II), preferably $\Delta^1$-cortienic acid or $\Delta^1$-cortienic acid methyl ester, together with sodium chloride, polysorbate 80 and 1 to 6 ounces of water (the water being added shortly before use). The suspension can be administered as a retention enema or by continuous drip several times weekly in the treatment of ulcerative colitis.

Another exemplary formulation is a sterile, multiple dose antibiotic and steroid combination suspension for topical ophthalmic use. Each mL of suspension contains: as active ingredients, tobramycin 0.3% (3 mg) and loteprednol etabonate 0.5% (5 mg); as synergist, $\Delta^1$-cortienic acid 0.25 to 1.0% (2.5 to 10 mg); as preservative, benzalkonium chloride 0.01%; and as inactives tyloxapol, edetate disodium, sodium chloride, hydroxyethyl cellulose, sodium sulfate, sulfuric acid and/or sodium hydroxide (to adjust pH) and purified water.

Another example is a sterile, multiple dose antibiotic and steroid combination ointment for topical ophthalmic use. Each gram of ointment contains: as active ingredients, tobramycin 0.3% (3 mg) and loteprednol etabonate 0.2% (2 mg); as synergist, $\Delta^1$-cortienic acid methyl ester 0.2% to 1.0% (2 to 10 mg); as preservative, chlorobutanol 0.5%; and as inactives, mineral oil and white petrolatum.

Yet another exemplary formulation is a ophthalmic anti-infective/anti-inflammatory sterile suspension containing: as active ingredients, sulfacetamide sodium 10% and loteprednol etabonate (microfine suspension) 0.5%; as synergist, $\Delta^1$-cortienic acid methyl ester 0.5 to 1.5%; as preservative, benzalkonium chloride (0.004%); as inactives, polyvinyl alcohol 1.4%, polysorbate 80, edetate disodium, dibasic sodium phosphate, monobasic potassium phosphate, sodium thiosulfate, hydrochloric acid and/or sodium hydroxide to adjust the pH, and purified water. A similar composition may be formulated for otic administration.

Another ophthalmic ointment containing an antibacterial and a corticosteroid is exemplified by a sterile ointment containing: as actives, sulfacetamide sodium 10% and loteprednol etabonate, 0.2%; as synergist, $\Delta^1$-cortienic acid, 0.1% to 1.0%; as preservative, phenylmercuric acetate (0.0008%); and as inactives, mineral oil, white petrolatum, and petrolatum and lanolin alcohol.

Another example of a sterile ophthalmic formulation is a topical anti-inflammatory/anti-infective suspension containing, as active ingredients, loteprednol etabonate (microfine suspension) 0.5%, neomycin sulfate equivalent to 0.35% neomycin base, polymyxin B sulfate 10,000 units/mL; as synergist, $\Delta^1$-cortienic acid methyl ester, 0.25 to 1.0%; as preservative, thimerosal 0.001%; and as inactive ingredients, polyvinyl alcohol 1.4%, polysorbate 80, propylene glycol, sodium acetate and purified water.

Yet another illustrative sterile ophthalmic suspension which is a topical anti-inflammatory/anti-infective combination product contains: as active ingredients, gentamicin sulfate equivalent to 0.3% gentamicin base and loteprednol etabonate (microfine suspension) 0.5%; as synergist, $\Delta^1$-cortienic acid or its methyl ester, 0.5 to 1.0%; as preservative, benzalkonium chloride 0.005%; as inactive ingredients, polyvinyl alcohol 1.4%, edetate disodium, hydroxypropyl methylcellulose, polysorbate 80, sodium citrate dihydrate, sodium chloride and purified water. The composition may contain sodium hydroxide and/or hydrochloric acid to adjust the pH to be in the range of 5.5 to 6.6.

Another sterile ophthalmic suspension formulation contains, per mL: as active, loteprednol etabonate 2 mg (0.2%); as synergist, $\Delta^1$-cortienic acid methyl ester 0.5 to 5 mg (0.05 to 0.5%); as preservative, benzalkonium chloride 0.01%; as inactives, edetate disodium, glycerin, povidone, purified water and tyloxapol. Hydrochloric acid and/or sodium hydroxide may be added to adjust the pH to 5.3 to 5.6.

Yet another sterile ophthalmic suspension formulation contains, per mL: as active ingredient, loteprednol etabonate 5 mg (0.5%); as synergist, $\Delta^1$-cortienic acid 5 to 15 mg (0.5 to 1.5%); as preservative, benzalkonium chloride 0.01%; as inactive ingredients, edetate disodium, glycerine, povidone, purified water and tyloxapol. Hydrochloric acid and/or sodium hydroxide may be added to adjust the pH to 5.3 to 5.6.

For dermatological use, in the treatment of fungal infections with associated inflammation, a cream or lotion combining clotrimazole, a synthetic antifungal agent, a compound of formula (I) and a compound of formula (II) may be formulated. A suitable cream or lotion contains, in each gram of cream or lotion: 10 mg of clotrimazole, 0.5 mg of loteprednol etabonate and 0.25 to 2.0 mg of $\Delta^1$-cortienic acid, in a hydrophilic cream or lotion base consisting of purified water, mineral oil, white petrolatum, cetearyl alcohol 70/30, ceteareth-30, propylene glycol, sodium phosphate monobasic monohydrate and phosphoric acid, with benzyl alcohol as a preservative. If necessary, the lotion may contain sodium hydroxide.

Capsules or tablets suitable for oral administration in the treatment of Crohn's disease may be formulated to protect the compounds of formulas (I) and (II) from gastric juice and to dissolve when they reach a higher pH in the duodenum. In one formulation of this type, each capsule contains 5-20 mg of micronized loteprednol etabonate, 5-80 mg of micronized $\Delta^1$-cortienic acid methyl ester (in a weight ratio of 1:1 to 4:1 of $\Delta^1$-cortienic acid methyl ester to loteprednol etabonate), with ethyl cellulose, acetyl tributyl citrate, methacrylic acid copolymer type C, triethyl citrate, antifoam M, polysorbate 80, talc and sugar spheres, in a shell composed of gelatin, iron oxide and titanium oxide. The granules in the formulation are coated to prevent dissolution in gastric juice but dissolve at pH>5.5, normally when the granules reach the duodenum. After that, a matrix of ethyl cellulose with the steroids releases them in a time-dependent manner in the intestinal lumen.

For the treatment of asthma, a sterile suspension for oral inhalation via a compressed air-driven jet nebulizer may be formulated. The suspension contains, as the active ingredient, micronized loteprednol etabonate; as the enhancing agent, micronized $\Delta^1$-cortienic acid or $\Delta^1$-cortienic acid methyl ester (in a 0.5:1 to 2:1 weight ratio to loteprednol etabonate); and as inactives, disodium edetate, sodium chloride, sodium citrate, citric acid, polysorbate 80, and water for injection. Single dose ampules contain 0.5, 1.0, 1.5 and 2.0 mg of loteprednol etabonate.

An alternate preparation for the treatment of asthma is an inhalation-driven multidose dry powder inhaler containing only micronized loteprednol etabonate and micronized $\Delta^1$-cortienic acid. Each actuation is designed to provide 400 mcg of loteprednol etabonate and 500 mcg of $\Delta^1$-cortienic acid and to act directly on the respiratory tract.

For the treatment and management of nasal symptoms of seasonal or perennial allergic rhinitis, a nasal spray or gel may be used. One such nasal formulation is a metered-dose, manual pump spray containing a micronized suspension of loteprednol etabonate and $\Delta^1$-cortienic acid methyl ester in an aqueous medium. The medium also contains microcrystalline cellulose and carboxymethyl cellulose sodium, anhydrous dextrose, polysorbate 80, disodium edetate, potassium sorbate and purified water, with hydrochloric acid added to adjust the pH to about 4.5. The formulation is designed to deliver 50 or 100 mcg of loteprednol etabonate and 50 to 150 or 100 to 300 mcg, respectively, of $\Delta^1$-cortienic acid methyl ester per spray.

To treat the pruritic and inflammatory manifestations of anti-inflammatory steroid-responsive dermatoses, especially localized lesions which are dry and scaly, a tape containing the active ingredient and enhancer may be used as both a vehicle and an occlusive dressing. One such product is a moisture-impervious plastic surgical tape containing loteprednol etabonate and $\Delta^1$-cortienic acid. Each square centimeter of tape contains 10 µg of loteprednol etabonate and 10 to 40 µg of $\Delta^1$-cortienic acid evenly distributed in the adhesive layer. The tape is made of polyethylene film, while the adhesive is a synthetic copolymer of acrylate ester and acrylic acid.

For the treatment of ulcerative colitis, a rectal suspension in a disposable single-dose enema may be formulated for ready self-administration. A typical disposable single dose unit for rectal administration contains 60 mL of suspension containing: 10-100 mg of loteprednol etabonate and 10-100 or 30-300 mg of $\Delta^1$-cortienic acid (in a 1:1 or 3:1 weight ratio to loteprednol etabonate) in an aqueous solution containing carbomer 934P, polysorbate 80, purified water, sodium hydroxide and methyl paraben.

For the treatment of superficial bacterial infections of the external auditory canal and treatment of infections of mastoidectomy and fenestration cavities accompanied by inflammation, an otic suspension may be used. One such suspension contains colistin sulfate and neomycin sulfate as antibiotics, the selected steroids of formulas (I) and (II) and thonzonium bromide, a surface-active agent; for example, a suspension which contains, per mL: colistin base activity, 3 mg (as the sulfate); neomycin base activity, 3.3 mg (as the sulfate); loteprednol etabonate, 10 mg (1%); $\Delta^1$-cortienic acid, 10 to 40 mg (1 to 4%), thonzonium bromide, 0.5 mg (0.5%), polysorbate 80, acetic acid and sodium acetate in a buffered aqueous vehicle. Thimerosal (0.002%) is added as a preservative. The suspension is buffered at pH 5.

A foam may be formulated for use in the treatment of inflammatory and pruritic manifestations of corticosteroid-responsive dermatoses of the anal region. An exemplary foam contains 1% loteprednol etabonate, 0.5 to 3% Δ¹-cortienic acid methyl ester, and 1% pramoxine hydrochloride (a local anaesthetic) in a hydrophilic base containing cetyl alcohol, emulsifying wax, methyl paraben, polyoxyethylene-10 stearyl ether, propylene glycol, propyl paraben, purified water, trolamine, ☐sobutene and propane.

For intramuscular, intrasynovial, soft tissue or intralesional injection for various conditions, especially for intrasynovial or soft tissue injection as therapy in synovitis of osteoarthritis, rheumatoid arthritis, acute and subacute bursitis, acute gouty arthritis, epicondylitis, acute nonspecific tenosynovitis and post-traumatic osteoarthritis, a sterile aqueous suspension may be formulated. Each mL of suspension contains 20, 40 or 80 mg/mL of loteprednol etabonate; and 20, 40 or 80 or 40, 80 or 160 mg/mL, respectively, of Δ¹-cortienic acid methyl ester; together with polyethylene glycol 3350, polysorbate 80, monobasic sodium phosphate, dibasic sodium phospate USP, benzyl alcohol (as preservative), sodium chloride (to adjust tonicity) and when necessary to adjust pH to within 3.5 to 7.0, sodium hydroxide and/or hydrochloric acid.

For use in the treatment of inflamed hemorrhoids, post irradiation proctitis, as an adjunct in the treatment of chronic ulcerative colitis, cryptitis, other inflammatory conditions of the anorectum and pruritus ani, suppositories may be formulated. One such suppository contains 10-25 mg loteprednol etabonate and 10-25 or 40-100 mg Δ¹-cortienic acid (in a 1:1 or 4:1 weight ratio to the loteprednol etabonate) in a hydrogenated cocoglyceride base.

For relief of the inflammatory and pruritic manifestations of corticosteroid-responsive dermatoses of the anal region, a rectal cream may be used. An illustrative rectal cream contains 1% loteprednol etabonate, 1% Δ¹-cortienic acid methyl ester and 1% pramoxine hydrochloride (a topical anaesthetic) in a washable, nongreasy base containing stearic acid, cetyl alcohol, aquaphor, isopropyl palmitate, polyoxyl 40 stearate, propylene glycol, potassium sorbate 0.1%, sorbic acid 0.1%, triethanolamine, lauryl sulfate and water.

For various dermal conditions having both an inflammatory/pruritic component and a fungal/bacterial component, a topical cream composition may be formulated to contain a compound of formula (I), a compound of formula (II) and iodoquinol (as an antifungal and antibacterial agent). An illustrative cream contains, per gram, 10 mg of loteprednol etabonate, 5 to 20 mg of Δ¹-cortienic acid and 10 mg of iodoquinol in a greaseless base of purified water, propylene glycol, glyceryl monostearate SE, cholesterol and related sterols, isopropyl myristate, polysorbate 60, cetyl alcohol, sorbitan monostearate, polyoxyl 40 stearate, sorbic acid and polysorbate 20.

Another topical preparation for dermatological use in treating conditions with an inflammatory/pruritic component and a fungal/bacterial component may be formulated to contain a compound of formula (I), a compound of formula (II) and iodochlorhydroxyquin (also known as clioquinol), which has antifungal and antibacterial properties. These ingredients are, for example, formulated as a cream, ointment or lotion containing 3% iodochlorhydroxyquin, 0.5% or 1.0% loteprednol etabonate and 0.5-2.0% or 1.0-4.0%, respectively, Δ¹-cortienic acid methyl ester.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:
1. A combination comprising:
(a) a compound having the formula:

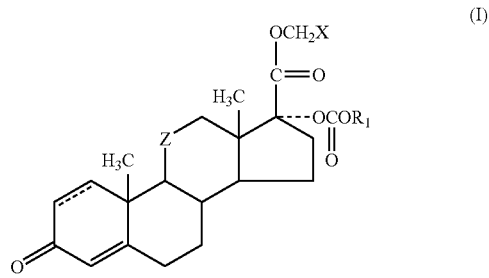

wherein:
$R_1$ is $C_1$-$C_7$ alkyl;
Z is carbonyl or β-hydroxymethylene;
X is Cl or F;
and the dotted line in ring A indicates that the 1,2-linkage is saturated or unsaturated; and
(b) a compound having the formula:

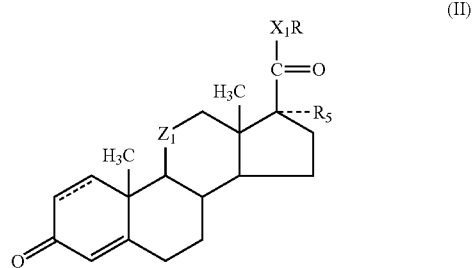

wherein:
R is H or $C_1$-$C_4$ alkyl;
$Z_1$ is carbonyl or β-hydroxymethylene;
$X_1$ is —O— or —S—;
$R_5$ is —OH, —OR$_6$, —OCOOR$_6$ or —OCOR$_7$ wherein $R_6$ is $C_1$-$C_4$ alkyl and $R_7$ is $C_1$-$C_4$ alkyl, fluoromethyl or chloromethyl;
and the dotted line is defined as above;
with the proviso that when R is $C_1$-$C_4$ alkyl, then $R_5$ is —OH;
in a combined synergistic anti-inflammatory effective amount;
the amount of compound of formula (II) being sufficient to enhance the anti-inflammatory activity or duration of action, or both, of said compound of formula (I);
with the proviso that [3H]-triamcinolone acetonide is excluded from the combination.

2. A combination according to claim 1, wherein the compound of formula (I) is:
(a) chloromethyl 17α-ethoxycarbonyloxy-11β-hydroxyandrosta-1,4-dien-3-one-17β-carboxylate;
(b) chloromethyl 11β-hydroxy-17α-methoxycarbonyloxyandrost-4-en-3-one-17β-carboxylate;
(c) chloromethyl 17α-ethoxycarbonyloxy-11β-hydroxyandrost-4-en-3-one-17β-carboxylate;
(d) chloromethyl 17α-butoxycarbonyloxy-11β-hydroxyandrost-4-en-3-one-17β-carboxylate;

(e) chloromethyl 11β-hydroxy-17α-isopropoxycarbonyloxyandrost-4-en-3-one-17β-carboxylate;

(f) chloromethyl 11β-hydroxy-17α-isopropoxycarbonyloxyandrosta-1,4-dien-3-one-17β-carboxylate;

(g) chloromethyl-11β-hydroxy-17α-isobutoxycarbonyloxyandrost-4-en-3-one-17β-carboxylate;

(h) chloromethyl 11β-hydroxy-17α-propoxycarbonyloxyandrost-4-en-3-one-17β-carboxylate;

(i) fluoromethyl 11β-hydroxy-17α-isopropoxycarbonyloxyandrost-4-en-3-one-17β-carboxylate;

(j) chloromethyl 11β-hydroxy-17α-n-propoxycarbonyloxyandrosta-1,4-dien-3-one-17β-carboxylate; or (k) chloromethyl 11β-hydroxy-17α-methoxycarbonyloxyandrosta-1,4-dien-3-one-17β-carboxylate.

3. A combination according to claim 1, wherein, in the compound of formula (I), $R_1$ is methyl, ethyl, n-propyl, isopropyl, n-butyl or isobutyl, X is chloro and Z is β-hydroxymethylene.

4. A combination according to claim 3, wherein, in the compound of formula (I), the 1,2-linkage is unsaturated.

5. A combination according to claim 1, wherein the compound of formula (I) is loteprednol etabonate.

6. A combination according to claim 1, wherein the compound of formula (II) is:

(a) 11β,17α-dihydroxyandrost-4-en-3-one-17β-carboxylic acid;

(b) 11β,17α-dihydroxyandrosta-1,4-dien-3-one-17β-carboxylic acid;

(c) methyl 11β,17α-dihydroxyandrost-4-en-3-one-17β-carboxylate;

(d) ethyl 11β,17α-dihydroxyandrost-4-en-3-one-17β-carboxylate;

(e) methyl 11β,17α-dihydroxyandrosta-1,4-dien-3-one-17β-carboxylate; or (f) ethyl 11β,17α-dihydroxyandrosta-1,4-dien-3-one-17β-carboxylate.

7. A combination comprising loteprednol etabonate and a compound having the formula:

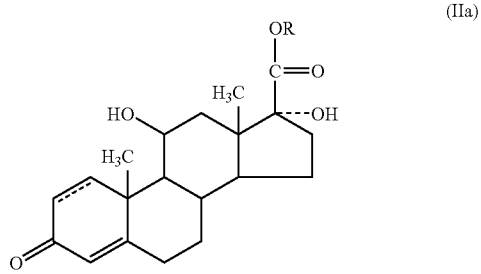

(IIa)

wherein R is H or $C_1$-$C_4$ alkyl and the dotted line in ring A indicates that the 1,2-linkage is saturated or unsaturated, in a combined synergistic anti-inflammatory effective amount, the amount of the compound of formula (IIa) being sufficient to enhance the anti-inflammatory activity or duration of action, or both, of loteprednol etabonate, with the proviso that [3H]-triamcinolone acetonide is excluded from the combination.

8. A combination according to claim 7, wherein, in the compound of formula (IIa), R is H, methyl or ethyl.

9. A combination according to claim 8, wherein the compound of formula (IIa) is 11β,17α-dihydroxyandrosta-1,4-dien-3-one-17β-carboxylic acid or methyl 11β,17α-dihydroxyandrosta-1,4-dien-3-one-17β-carboxylate.

10. A combination according to claim 7, wherein the molar ratio of compound of formula (IIa) to loteprednol etabonate is from about 5:1 to about 0.5:1.

11. A combination according to claim 8, wherein the molar ratio of compound of formula (IIa) to loteprednol etabonate is from about 5:1 to about 0.5:1.

12. A combination according to claim 9, wherein the molar ratio of compound of formula (IIa) to loteprednol etabonate is from about 5:1 to about 0.5:1.

13. A pharmaceutical composition comprising:

(1) a combined synergistic anti-inflammatory effective amount of:

(a) a compound having the formula:

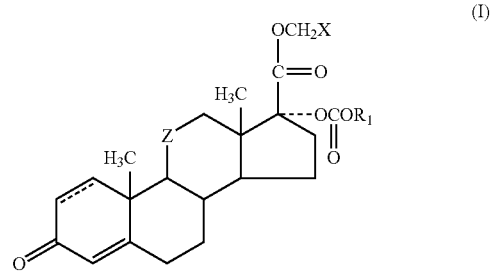

(I)

wherein:

$R_1$ is $C_1$-$C_7$ alkyl;

Z is carbonyl or β-hydroxymethylene;

X is Cl or F;

and the dotted line in ring A indicates that the 1,2-linkage is saturated or unsaturated;

and (b) a compound having the formula:

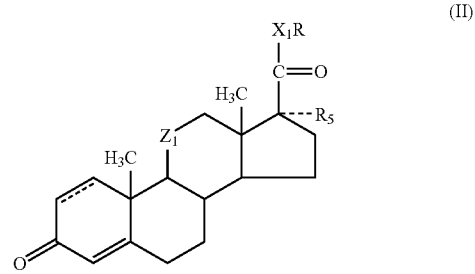

(II)

wherein:

R is H or $C_1$-$C_4$ alkyl;

$Z_1$ is carbonyl or β-hydroxymethylene;

$X_1$ is —O— or —S—;

$R_5$ is —OH, —$OR_6$, —$OCOOR_6$ or —$OCOR_7$ wherein $R_6$ is $C_1$-$C_4$ alkyl and $R_7$ is $C_1$-$C_4$ alkyl, fluoromethyl or chloromethyl;

and the dotted line is defined as above;

with the proviso that when R is $C_1$-$C_4$ alkyl, then $R_5$ is —OH;

the amount of compound of formula (II) being sufficient to enhance the anti-inflammatory activity or duration of action, or both, of said compound of formula (I); and (2) a non-toxic, pharmaceutically acceptable carrier therefor suitable for topical or other local application;

with the proviso that [3H]-triamincolone acetonide is excluded from the composition.

14. A composition according to claim 13, wherein the compound of formula (I) is:
(a) chloromethyl 17α-ethoxycarbonyloxy-11β-hydroxyandrosta-1,4-dien-3-one-17β-carboxylate;
(b) chloromethyl 11β-hydroxy-17α-methoxycarbonyloxyandrost-4-en-3-one-17β-carboxylate;
(c) chloromethyl 17α-ethoxycarbonyloxy-11β-hydroxyandrost-4-en-3-one-17β-carboxylate;
(d) chloromethyl 17α-butoxycarbonyloxy-11β-hydroxyandrost-4-en-3-one-17β-carboxylate;
(e) chloromethyl 11β-hydroxy-17α-isopropoxycarbonyloxyandrost-4-en-3-one-17β-carboxylate;
(f) chloromethyl 11β-hydroxy-17α-isopropoxycarbonyloxyandrosta-1,4-dien-3-one-17β-carboxylate;
(g) chloromethyl-11β-hydroxy-17α-isobutoxycarbonyloxyandrost-4-en-3-one-17β-carboxylate;
(h) chloromethyl 11β-hydroxy-17α-propoxycarbonyloxyandrost-4-en-3-one-17β-carboxylate;
(i) fluoromethyl 11β-hydroxy-17α-isopropoxycarbonyloxyandrost-4-en-3-one-17β-carboxylate;
(j) chloromethyl 11β-hydroxy-17α-n-propoxycarbonyloxyandrosta-1,4-dien-3-one-17β-carboxylate; or
(k) chloromethyl 11β-hydroxy-17α-methoxycarbonyloxyandrosta-1,4-dien-3-one-17β-carboxylate.

15. A composition according to claim 13, wherein, in the compound of formula (I), $R_1$ is methyl, ethyl, n-propyl, isopropyl, n-butyl or isobutyl, X is chloro and Z is β-hydroxymethylene.

16. A composition according to claim 15, wherein, in the compound of formula (I), the 1,2-linkage is unsaturated.

17. A composition according to claim 13, wherein the compound of formula (I) is loteprednol etabonate.

18. A composition according to claim 13, wherein, in the compound of formula (II), $R_5$ is —OH.

19. A composition according to claim 13, wherein the compound of formula (II) is:
(a) 11β,17α-dihydroxyandrost-4-en-3-one-17β-carboxylic acid;
(b) 11β,17α-dihydroxyandrosta-1,4-dien-3-one-17β-carboxylic acid;
(c) methyl 11β,17α-dihydroxyandrost-4-en-3-one-17β-carboxylate;
(d) ethyl 11β,17α-dihydroxyandrost-4-en-3-one-17β-carboxylate;
(e) methyl 11β,17α-dihydroxyandrosta-1,4-dien-3-one-17β-carboxylate; or
(f) ethyl 11β,17α-dihydroxyandrosta-1,4-dien-3-one-17β-carboxylate.

20. A pharmaceutical composition comprising:
(1) a combined synergistic anti-inflammatory effective amount of:
(a) loteprednol etabonate; and
(b) a compound having the formula:

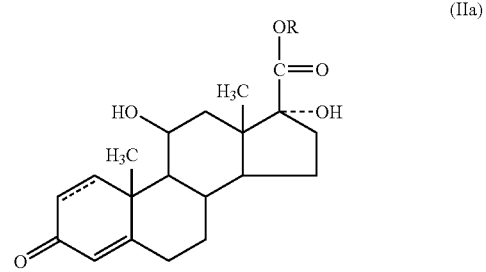

wherein R is H or $C_1$-$C_4$ alkyl and the dotted line in ring A indicates that the 1,2-linkage is saturated or unsaturated, the amount of compound of formula (IIa) being sufficient to enhance the anti-inflammatory activity or duration of action, or both, of loteprednol etabonate; and
(2) a non-toxic, pharmaceutically acceptable carrier therefor suitable for topical or other local application;
with the proviso that [3H]-triamcinolone acetonide is excluded from the composition.

21. A composition according to claim 20, wherein, in the compound of formula (IIa), R is H, methyl or ethyl.

22. A composition according to claim 21, wherein the compound of formula (IIa) is 11β,17α-dihydroxyandrosta-1,4-dien-3-one-17β-carboxylic acid or methyl 11β,17α-dihydroxyandrosta-1,4-dien-3-one-17β-carboxylate.

23. A composition according to claim 20, wherein the molar ratio of compound of formula (IIa) to loteprednol etabonate is from about 5:1 to about 0.5:1.

24. A composition according to claim 21, wherein the molar ratio of compound of formula (IIa) to loteprednol etabonate is from about 5:1 to about 0.5:1.

25. A composition according to claim 22, wherein the molar ratio of compound of formula (IIa) to loteprednol etabonate is from about 5:1 to about 0.5:1.

26. A composition according to claim 13, wherein the carrier is ophthalmically acceptable and the composition is an ophthalmic composition.

27. A composition according to claim 13, formulated as: an ointment, gel, lotion or cream; a powder; drops or a spray; a suppository, retention enema or foam; a chewable or suckable tablet or pellet; an aerosol; a nebulized or powdered formulation for oral inhalation; a parenteral or other injectable dosage form; or an oral dosage form which releases the active ingredients in the upper or lower intestines.

28. A composition according to claim 20, formulated as: an ointment, gel, lotion or cream; a powder; drops or a spray; a suppository, retention enema or foam; a chewable or suckable tablet or pellet; an aerosol; a nebulized or powdered formulation for oral inhalation; a parenteral or other injectable dosage form; or an oral dosage form which releases the active ingredients in the upper or lower intestines.

* * * * *